United States Patent [19]

Yamada et al.

[11] Patent Number: 5,683,709
[45] Date of Patent: Nov. 4, 1997

[54] POLY(BENZALKONIUM SALT) AS AN ANTIMICROBIAL AGENT FOR AQUEOUS DRUG COMPOSITIONS

[75] Inventors: Akira Yamada, Claremont; Teresa H. Kuan, Placentia; Ajay Vasudev Pandurangi, Alta Loma, all of Calif.

[73] Assignee: CIBA Vision Corporation, Duluth, Ga.

[21] Appl. No.: 238,560

[22] Filed: May 5, 1994

[51] Int. Cl.$^6$ .................................................. A01N 25/10
[52] U.S. Cl. .................... 424/409; 424/78.1; 424/78.11; 424/78.12; 424/78.08
[58] Field of Search .............................. 604/262, 265, 604/295, 339, 349, 357, 408; 428/321.1, 35.2; 424/78.1, 78.11, 78.12, 409, 422, 428, 455; 514/58, 357, 643

[56] References Cited

U.S. PATENT DOCUMENTS

| | | | |
|---|---|---|---|
| 3,843,782 | 10/1974 | Krezanaski et al. | 424/78 |
| 4,271,143 | 6/1981 | Schwoenwald et al. | 424/78 |
| 4,349,646 | 9/1982 | Nudel et al. | 525/256 |
| 4,407,792 | 10/1983 | Schwoenwald et al. | 424/81 |
| 5,104,649 | 4/1992 | Jansson et al. | 424/78.31 |
| 5,192,780 | 3/1993 | York et al. | 514/357 |
| 5,300,287 | 4/1994 | Park | 424/78.04 |
| 5,324,718 | 6/1994 | Loftsson | 514/58 |
| 5,340,583 | 8/1994 | Dziabo et al. | 424/412 |
| 5,364,637 | 11/1994 | De et al. | 424/464 |

FOREIGN PATENT DOCUMENTS

| | | |
|---|---|---|
| 640737 | 1/1979 | European Pat. Off. . |
| 0334673 | 3/1989 | European Pat. Off. . |

*Primary Examiner*—Neil S. Levy
*Attorney, Agent, or Firm*—Michael U. Lee; R. Scott Meece

[57] ABSTRACT

A package containing an aqueous drug composition containing an insoluble resin comprising benzalkonium salt units in an amount sufficient to inhibit growth of microbes in said aqueous drug solution. Typically, the insoluble resin is a polymer having repeating units of the formula:

$$-[CH_2-CH(Ar)]-$$

wherein Ar=a group of the formula:

$$-Phe-CH_2-N^+(CH_3)_2R\ X^-$$

wherein R=long chain alkyl such as $C_{8-18}$ alkyl, Phe= phenylene, and $X^-$ is a pharmaceutically acceptable counter anion such as $Cl^-$.

19 Claims, No Drawings

POLY(BENZALKONIUM SALT) AS AN ANTIMICROBIAL AGENT FOR AQUEOUS DRUG COMPOSITIONS

The invention relates to the use of poly(benzalkonium salt) in aqueous drug compositions to inhibit microbial growth.

BACKGROUND OF THE INVENTION

Some patients are sensitive to the preservative in aqueous drug compositions, e.g., eye drops. For these patients, a preservative-free formulation is preferably used. A disadvantage of preservative-free formulations is, however, that once the package is opened the contents can deteriorate quickly because of microbial growth. Therefore, a preservative-free formulation is often packaged in a single or daily dose container, which is not cost effective.

In ophthalmic drug formulations, benzalkonium chloride (BAC), a benzyl quaternary ammonium compound having a higher aliphatic chain, is widely used as an anti-microbial agent because of its relatively low toxicity to humans. However, benzalkonium chloride often irritates the eye at concentrations higher than about 0.02 weight %. Some patients are sensitive to benzalkonium chloride at concentrations as low as about 0.01% when the formulation containing BAC is used chronically. Benzalkonium chloride is a composition having the formula:

$$Ph\text{-}CH_2\text{-}N^+(CH_3)_2R\ Cl^-$$

wherein R=long chain alkyl, e.g., $C_{8\text{-}18}$alkyl, and Ph=phenyl.

Most commonly used strongly basic styrenic anion-exchange resins have benzyltrimethyl ammonium functionality; the functional group has a similar structure to BAC except that the group does not have a higher aliphatic chain. Such resins are synthesized by chloromethylation of cross-linked polystyrene followed by a treatment with trimethylamine. These resins have good chemical stability; they are inert to strong acids, concentrated alkalies, hydrocarbons, alcohols, ethers, and other common solvents except for strong oxidants. The styrenic anion-exchange resins are used in many applications including deionization of water and purification of organic chemicals.

Cross-linked chloromethylated polystyrene, known as Merrifield resin, is also widely used as a supporting resin for solid phase peptide synthesis. Treatment of cross-linked chloromethylated polystyrene with a tertiary amine having dimethyl and a higher alkyl group, e.g. N,N-dimethyldodecylamine, can produce an insoluble polymer containing BAC functionality. Such resins have been synthesized and used for water disinfection by Nudel et al. (U.S. Pat. Nos. 4,349,646; 4,427,796 and 4,446,103). Recently, another patent was issued to Jansson et al. (U.S. Pat. No. 5,104,649) for "an article having a polyethylene surface and biologically active quaternary amine groups which are grafted to said surface by sulfonamide groups." The patentees stated that the polymer could be employed to inhibit microbial growth in the adjacent area of the polymer and as a disinfectant for fluids such as water. These patents, however, did not describe any application as an anti-microbial preservative for drug solutions. The mechanism of the bactericidal action of quaternary ammonium compounds such as BAC is closely related to the surface activity of the quaternary ammonium compound. It has been postulated that interaction of the bactericidal agent with the cell wall interferes with the metabolic process of the organism, and this causes the inhibition or killing action. (See, for instance, Richard A. Reck, "Encyclopedia of Chemical Technology," Third Ed., Vol. 19, John Wiley & Sons, 1982, p. 523.) In the case of insoluble biocidal polymer having surface-grafted quaternary ammonium groups, it is considered that the biocidal effect is limited to the adjacent area of the polymer surface. Therefore, these polymers were used in the form of a resin bed column (see the Nudel et al. patents cited above) or in the form of fine powder dispersed in the test medium with constant agitation for water disinfection (see the Jansson et al. patent, cited above).

The present invention is based on the discovery that the addition of insoluble poly(benzalkonium salt) to aqueous drug compositions is effective in inhibiting microbial growth, and that such effectiveness does not require constant agitation.

BRIEF SUMMARY OF THE INVENTION

The invention provides a package containing an aqueous drug composition, containing an insoluble resin comprising benzalkonium units in an amount sufficient to inhibit growth of microbes in said aqueous drug solution. Preferably, the aqueous drug composition is free of soluble quaternary ammonium anti-microbial agents.

DETAILED DESCRIPTION OF THE INVENTION

The insoluble resin employed in the invention contains repeating units of the formula:

$$[CH_2\text{-}CH(Ar)]\text{-}$$

wherein Ar=a group of the formula:

$$\text{-}Phe\text{-}CH_2\text{-}N^+(CH_3)_2R\ X^-$$

wherein R=long chain alkyl, e.g., $C_{8\text{-}18}$alkyl, Phe=phenylene, and $X^-$=a pharmaceutically acceptable counter anion such as halide (e.g., $Cl^-$, $Br^-$, $I^-$), acetate, benzoate, carbonate, citrate, formate, gluconate, glycolate, hydroxide, lactate, malate, maleate, malonate, nitrate, phosphate, propionate, succinate, sulfate, tartrate, and the like. The counter anion can be a multivalent ion; however, the counter ion will most probably exist in fact as a monovalent ion which will be associated with only one BAC unit counter cation. For instance, when an $SO_4^{2-}$ ion cannot associate with two BAC units of the polymeric chain because of steric hindrance, it will most likely exist as a monovalent anion such as $HSO_4^-$ or $NaSO_4^-$.

Such resins are prepared from polystyrene resins that are cross-linked, as with a small percentage (e.g., 1–10 weight percent) of divinylbenzene, and which have been treated to impart benzalkonium salt functionality. One method of preparing the BAC resins is to react chloromethylated polystyrene with an N,N-dimethyl($C_{8\text{-}18}$alkyl)amine. Another method is to react an N,N-dimethylamino polystyrene resin with a $C_{8\text{-}18}$alkyl chloride. A third method is to react an N,N-dimethylamino polystyrene resin with a $C_{8\text{-}18}$alkyl bromide (which is more reactive than the corresponding chloride), followed (if desired) by replacement of the $Br^-$ anion with a $Cl^-$, as by treatment first by aqueous sodium hydroxide and then by hydrochloric acid. These three alternative methods of preparing the BAC-containing resin are illustrated below:

MATERIALS

Merrifield Resin (chloromethylated polystyrene beads cross-linked with 3% divinylbenzene, 20–60 mesh, 4 meq Cl/g) was obtained from Polysciences, Inc: Cat #17409, Lot 60017. The resin, 100.01 g was soaked in 600 mL of acetone for 24 hours, separated by filtration, washed with acetone and resoaked in 600 mL of acetone for 65 hours. The resin was washed with acetone and methanol successively, and dried in vacuo to give 81.99 g of purified resin.

Amberlite® IRA-93 (an ion-exchange resin containing tertiary amine functionality) was purchased from Polysciences, Inc. The wet resin, 160.83 g was washed with 2 L of water and 300 mL of methanol and soaked in 500 mL of methanol overnight. The resin was washed again with methanol (2×300 mL) and soaked in 500 mL of methanol overnight. The resin was further washed with methanol (2×300 mL) and acetone (2×300 mL) and dried in vacuo to yield 58.8 g of purified resin.

A sample of DIAION WA-30 (an ion-exchange resin containing N,N-dimethylbenzylamine functionality) was obtained from Mitsubishi Kasei, Japan. The resin, 93.4 g, was soaked in 200 mL of methanol for 65 hours and then extracted with methanol using a Soxhlet extractor for 2 days. The resin was vacuum-dried to a constant weight of 55.6 g.

N,N-Dimethyldodecylamine (Cat #28,438-6, Lot 06514AY), 1-chlorohexadecane (Cat #24,562-3, Lot 02323CT) and 1-bromodo-decane (Cat #B6,555-1, Lot 06019BX) were purchased from Aldrich Chemical Company and used without further purification. Baker Analyzed HPLC grade anhydrous acetone (Cat #9002-03, Lot F28256) and methanol (Cat #9093-03, Lot F20259) were purchased from VWR Scientific and used as received. p-Dioxane (Baker Analyzed reagent, Cat #3-9231, Lot 052337) was distilled from lithium aluminum hydride.

PREPARATION OF POLY(BENZALKONIUM CHLORIDE) (PBAC) BEADS

A. From Merrifield Resin

Merrifield Resin, 70.00 g (280 mmol of Cl) was dispersed in 350 mL of anhydrous acetone and 154 mL (560 mmol) of N,N-dimethyldodecylamine was added to the dispersion under a nitrogen blanket. Then, the mixture was heated at reflux temperature for 7 hours and allowed to cool to room temperature. The product was separated by filtration, washed with acetone, and extracted with acetone for 24 hours using a Soxhlet extractor. The resin was further washed with methanol (3×200 mL) and water (3×200 mL) and then soaked in 1 L of water overnight. The resin was washed again with water (5×200 mL), methanol (3×200 mL), water (3×200 mL), methanol (3×200 mL) and acetone (3×150 mL) successively, and dried in vacuo to a constant weight of 127.07 g.

From the weight increase the quaternary ammonium group content of the product was calculated to be 2.10 mmol/g. The result was in good agreement with the elemental analysis of the product which showed 2.82% of nitrogen (2.01 mmol/g). The IR spectrum of the product showed that the characteristic peak at 1263 $c^{-1}$ assigned to $\delta_{CH}$ of the chloromethyl group in the starting resin diminished after the treatment and that the spectrum was very similar to that of monomeric BAC.

B. From Tertiary Amine Resin, IRA-93

A mixture of 18.15 g (>76.23 meq) of dry IRA-93, 100 mL of acetone and 50 mL (166 mmol) of 1-chlorohexadecane was heated at reflux temperature for 7 hours under a nitrogen blanket. The resin was extracted with acetone for 24 hours and with methanol for 24 hours using a Soxhlet extractor. After vacuum drying, the resin weighed 21.35 g. From the weight increase the quaternary ammonium content was calculated to be 0.57 mmol/g. This corresponds to the substitution of 16%. The low substitution may be due to the lower reactivity of alkyl chloride than benzyl chloride (Merrifield resin has benzyl chloride functionality).

C. From N,N-Dimethylbenzylamine Resin, WA30

A dry resin of WA-30, 22.35 g (103 meq) was allowed to swell in 100 mL of acetone for 1 hour and 50 mL (208 mmol) of 1-bromododecane was added slowly. Then, the mixture was heated at reflux temperature for 24 hours under a nitrogen blanket. The resin was extracted with acetone for 2 days using a Soxhlet extractor. After drying, the resin weighed 31.19 g. The weight increase corresponds to the functionality of 1.14 mmol/g, a substitution of 34%. The resin was retreated with 30 mL (125 mmol) of 1-bromododecane in 100 mL of p-dioxane at 88°–92° C. for 45 hours under nitrogen. Then the resin was washed with p-dioxane, extracted with acetone in a Soxhlet extractor for 26 hours and dried in vacuo to a constant weight of 34.38 g. The functionality was increased to 1.40 mmol/g by the second treatment (47% substitution).

The resin was converted to the chloride form by washing it with aqueous 2N sodium hydroxide, water, 1N hydrochloric acid, and water, successively.

Several batches of PBAC were prepared by the routes described above. Table 1, below, summarizes the results. The functionality (quaternary ammonium group content) of the samples was calculated from the weight increase by the reaction and the nitrogen or chlorine content of the product. Both calculations gave comparable results.

TABLE 1

Preparation of Poly(Benzalkonium Chloride)

| Example No. | Starting Resin Type | Quantity (g) | Yield (g) | Functionality (mmol/g) Gravimetric[a] | Elemental[b] |
|---|---|---|---|---|---|
| 1 | Merrifield | 10.0 | 18.12 | 2.10 | 2.10 |
| 2 | Merrifield | 10.29 | 18.95 | 2.14 | 2.38 |
| 3 | Merrifield | 70.00 | 127.07 | 2.10 | 2.01 |
| 4 | Merrifield | 133.66 | 249.74 | 2.18 | 2.30 |
| 5 | Merrifield | 48.36 | 89.63 | 2.16 | 2.16 |
| 6 | Merrifield | 49.11 | 88.47 | 2.08 | 1.93 |
| 7 | IRA-93 | 18.15 | 21.35 | 0.57 | — |
| 8 | WA-30 | 22.35 | 31.19 | 1.14[c] | — |
| 8R[d] | — | — | 34.38 | 1.40[e] | 1.42[e] |

[a]Calculated from the weight increase.
[b]Calculated from the nitrogen analysis.
[c]As bromide.
[d]The product of No. 8 was retreated.
[e]Calculated from the chlorine analysis.

ANTI-MICROBIAL EFFICACY OF PBAC

In order to test the anti-microbial efficacy of PBAC beads, produced as described above, a series of preservative effectiveness tests ("PET's") were run, as follows (the results of the tests are shown below in Table 2):

The first test (PET #2302) was performed in 0.9% saline using five microorganisms (*Staphylococcus aureus, Escherichia coli, Pseudomonas aeruginosa, Aspergillus niger and Candida albicans*) at the level of 0.1 g of resin per 1 mL medium with continuous agitation. The second test (PET #2320) was carried out in PBS (phosphate buffered saline)

using S. aureus and A. niger at the same level of resin concentration without agitation. The tests passed the USP and the BP (British pharmacopeia) B criteria but failed in the BP A criteria which require a quicker action in the biocidal effect than the other two criteria. In the J & J criteria the first test showed marginal results (failed only for A. niger) but the second test failed. (The USP, BP and J & J requirements are shown in Appendix 1, below.) These results suggest that the diffusion of microorganisms to the resin active sites is the rate determining step of the biocidal action. However, it is encouraging that the resin passed the USP and the BP B criteria even without continuous agitation. The third test (PET #2337) was conducted using three microorganisms at the resin concentration level of 0.3 g/mL without agitation to see the effect of the amount of the resin. The results showed that the three times increase in the resin concentration was still not enough to clear J & J and BP A criteria level requirements. A full preservative effectiveness test, Experiments PET #2388 and #2389, was carried out in order to determine the efficacy of PBAC in Hypotears®, a synthetic tear fluid used to lubricate and/or hydrate the eye. [Hypotears contains 1% polyvinyl alcohol in polyethylene glycol 400, dextrose, edetate disodium and purified water. The multi-dose commercial product contains benzalkonium chloride as a preservative.] The results showed that PBAC resin was also effective in Hypotears.

After the first test (PET #2302) was completed, the supernatant was analyzed by HPLC and the analysis did not detect any free benzalkonium chloride in the supernatant. However, the result does not guarantee that there was no leachable material which may have had biocidal effects. To identify whether the resin releases any material having biocidal effects or that the biocidal effect is exclusively obtained by the active sites on the resin, suspensions of the resin in PBS were continuously agitated at ambient temperature for prescribed periods of time to extract the resin with PBS and the supernatants were subjected to a preservative effectiveness test. The 24-hour extraction samples (PET #'s 2360 and 2361) showed that the presence of PBAC beads was important to realize the biocidal effects and that once the resin was removed the supernatant did not show effective kill as compared to the results of PET #s 2417 and 2419. However, a reduction of S. aureus was observed in the 24-hour extract after 14 days during the preservative effectiveness test, thus the results of PET #2361 showed that the supernatant passed the USP criteria. Also a faster reduction of S. aureus was observed in the 28-day extract. But these reductions are probably due to a natural reduction, since sometimes the natural reduction of S. aureus was observed even in PBS, as shown in the results of PET #2393. To confirm that no biocidal reagents are released from the resin, three more PBAC samples (Example Nos. 4, 5 and 6) were suspended in PBS (12-g resin/60-mL PBS) at 40° C. for 1 day and 7 days. The supernatant liquids were divided into two portions and inoculated with S. aureus and A. niger. After 24 hours of the inoculation, no significant reduction of the microorganisms was observed in all the supernatant liquids and in the control PBS. These results confirmed that the PBAC resin did not release any significant amounts of biocidal reagents.

MINIMUM EFFECTIVE CONCENTRATION OF PBAC AND EFFECT OF AGITATION

Experiments PET #'s 2412-2427 were carried out in order to determine the minimum quantity of the PBAC resin to be effective and to find the effect of agitation. As a preservative effectiveness test the experiments were carried out in an abbreviated version using only Staphylococcus aureus and Aspergillus niger instead of using all of the FDA required five organisms. The results are summarized in Table 2.

The data show that the PBAC resin effectively killed S. aureus at 0.2 g/mL level and the results passed the BP B criteria and the USP requirements. When the system was continuously agitated, the resin showed higher efficiency and attained the BP A criteria. As the resin concentration decreased to 0.1 g/mL, 0.05 g/mL and 0.025 g/mL, the rate of kill became slower. However, all the cases still passed the BP B criteria and the USP. The condition with continuous agitation showed a higher rate of kill as compared to the conditions without agitation at all the concentrations.

As for A. niger, the PBAC resin passed even the BP A criteria at 0.2 g/mL level whether the system was agitated or not, although the rate of kill was slower when no agitation was given. At 0.1 g/mL level the resin attained the BP B criteria with continuous agitation. Without agitation the resin failed to pass the BP B criteria but passed the USP. At 0.05 g/mL level the resin barely passed the USP. At 0.025 g/mL level the resin passed the USP barely only when no agitation was given. The effect of agitation was not significant at these two low concentrations of resin, although no-agitation conditions gave a little faster kill in the early stage. These results seemed strange, because the resin showed higher efficiency when the system was agitated in all other cases. These results can be explained if agitation somehow accelerated the growth of A. niger. A. niger has a structure of long filaments and the filaments could break up further to create more cells by agitation. Therefore, when a vigorous agitation is continuously given, the competitions between killing and producing more cells may be characteristics of this system for fungi such as A. niger. At low concentration of resin, the power of kill was reduced and thus the effect of cell generation may have become visible.

In conclusion, agitation increased the rate of kill but without agitation the resin was still effective as a preservative. The minimum required amounts of the PBAC resin to attain the USP and the BP B criteria Were 0.05 g/mL and 0.2 g/mL, respectively.

TABLE 2

Preservative Effectiveness Test Results of Poly(benzalkonium Chloride)

| PET# | Example No. Resin | Formula | BAC Unit Conc., % | Condition | Organism | PET Result[a] US/BB/BA/J |
|---|---|---|---|---|---|---|
| 2302 | 1 | 2.0 g/20 mL 0.9% NaCl | 7.1 | Cont. Shaking | S. Aureus | P/P/F/P |
| 2302 | 1 | 2.0 g/20 mL 0.9% NaCl | 7.1 | Cont. Shaking | E. Coli | P/P/P/P |
| 2302 | 1 | 2.0 g/20 mL 0.9% NaCl | 7.1 | Cont. Shaking | P. Aeruginosa | P/P/P/P |
| 2302 | 1 | 2.0 g/20 mL 0.9% NaCl | 7.1 | Cont. Shaking | A. Niger | P/P/F/F |
| 2302 | 1 | 2.0 g/20 mL 0.9% NaCl | 7.1 | Cont. Shaking | C. Albicans | P/P/P/P |
| 2320 | 1 | 2.0 g/20 mL PBS (150 mM) | 7.1 | No shaking | S. Aureus | P/P/F/F |
| 2320 | 1 | 2.0 g/20 mL PBS | 7.1 | No shaking | A. Niger | P/P/F/F |

TABLE 2-continued

Preservative Effectiveness Test Results of Poly(benzalkonium Chloride)

| PET# | Example No. Resin | Formula | BAC Unit Conc., % | Condition | Organism | PET Result* US/BB/BA/J |
|---|---|---|---|---|---|---|
| 2337 | 2 | 6.0 g/20 mL PBS | 24 | No Shaking | S. Aureus | P/P/F/F |
| 2337 | 2 | 6.0 g/20 mL PBS | 24 | No Shaking | A. Niger | P/F/F/F |
| 2337 | 2 | 6.0 g/20 mL PBS | 24 | No Shaking | P. Aeruginosa | P/P/F/F |
| 2360 | 3 | 2.5 g/25 mL PBS | 6.8 | 24 hr extract | A. Niger | F/F/F/F |
| 2361 | 3 | 2.5 g/25 mL PBS | 6.8 | 24 hr extract | S. Aureus | P/F/F/F |
| 2364 | 3 | 2.5 g/25 mL PBS | 6.8 | 28 day extract | S. Aureus | P/P/F/P |
| 2365 | 3 | 2.5 g/25 mL PBS | 6.8 | 28 day extract | A. Niger | F/F/F/F |
| 2388 | — | Hypotears w/o BAC | — | Control | S. Aureus | F/F/F/F |
| 2388 | — | Hypotears w/o BAC | — | Control | E. Coli | F/F/F/F |
| 2388 | — | Hypotears w/o BAC | — | Control | P. Aeruginosa | P/P/P/P |
| 2388 | — | Hypotears w/o BAC | — | Control | A. Niger | F/F/F/F |
| 2388 | — | Hypotears w/o BAC | — | Control | C. Albicans | F/F/F/F |
| 2389 | 3 | 6 g/20 mL Hypotears Multidose w/o BAC | 20.4 | No Shaking | S. Aureus | P/P/F/P |
| 2389 | 3 | 6 g/20 mL Hypotears Multidose w/o BAC | 20.4 | No Shaking | E. Coli | P/P/P/P |
| 2389 | 3 | 6 g/20 mL Hypotears Multidose w/o BAC | 20.4 | No Shaking | P. Aeruginosa | P/P/P/P |
| 2389 | 3 | 6 g/20 mL Hypotears Multidose w/o BAC | 20.4 | No Shaking | A. Niger | P/P/F/F |
| 2389 | 3 | 6 g/20 mL Hypotears Multidose w/o BAC | 20.4 | No Shaking | C. Albicans | P/P/P/P |
| 2393 | — | PBS | 0 | Control | S. Aureus | P/F/F/F |
| 2393 | — | PBS | 0 | Control | A. Niger | F/F/F/F |
| 2412 | 3 | 4 g/20 mL PBS | 13.6 | Shaking | S. Aureus | P/P/F/P |
| 2413 | 3 | 4 g/20 mL PBS | 13.6 | No Shaking | S. Aureus | P/P/F/P |
| 2414 | 3 | 4 g/20 mL PBS | 13.6 | Shaking | A. Niger | P/P/P/P |
| 2415 | 3 | 4 g/20 mL PBS | 13.6 | No Shaking | A. Niger | P/P/P/P |
| 2416 | 3 | 2 g/20 mL PBS | 6.8 | Shaking | S. Aureus | P/P/F/P |
| 2417 | 3 | 2 g/20 mL PBS | 6.8 | No Shaking | S. Aureus | P/P/F/P |
| 2418 | 3 | 2 g/20 mL PBS | 6.8 | shaking | A. Niger | P/P/F/F |
| 2419 | 3 | 2 g/20 mL PBS | 6.8 | No Shaking | A. Niger | P/P/F/F |
| 2420 | 3 | 1 g/20 mL PBS | 3.4 | Shaking | S. Aureus | P/P/F/P |
| 2421 | 3 | 1 g/20 mL PBS | 3.4 | No Shaking | S. Aureus | P/P/F/F |
| 2422 | 3 | 1 g/20 mL PBS | 3.4 | Shaking | A. Niger | P/F/F/F |
| 2423 | 3 | 1 g/20 mL PBS | 3.4 | No Shaking | A. Niger | P/F/F/F |
| 2424 | 3 | 0.5 g/20 mL PBS | 1.7 | Shaking | S. Aureus | P/P/F/F |
| 2425 | 3 | 0.5 g/20 mL PBS | 1.7 | No Shaking | S. Aureus | P/P/F/F |
| 2426 | 3 | 0.5 g/20 mL PBS | 1.7 | Shaking | A. Niger | F/F/F/F |
| 2427 | 3 | 0.5 g/20 mL PBS | 1.7 | No Shaking | A. Niger | P/F/F/F |
| 2538 | 3 | 5 g/25 mL Levo[b] | 13.6 | No Shaking | S. Aureus | P/P/F/P |
| 2539 | 3 | 5 g/25 mL Levo[b] | 13.6 | No Shaking | A. Niger | P/P/F/F |
| 2540 | — | Levo solution[b] | 0 | No Shaking | S. Aureus | P/F/F/F |
| 2540 | — | Levo solution[b] | 0 | No Shaking | A. Niger | P/P/P/P |

*US: USP criteria. BB: BP B criteria. BA: BP A criteria. J: J&J criteria. P: passed. F: failed.
[b]0.05% levocabastine, 7.5% hydroxypropyl-β-cyclodextrin (HP-β-CD), 1.0% boric acid, 0.25% sodium chloride, and 0.01% EDTA.

EFFICACY OF PBAC IN THE PRESENCE OF HP-β-CD

A complexing agent, such as hydroxypropyl-β-cyclodextrin (HP-β-CD) or other cyclodextrin derivatives which are well known in the art, can be used for solubilizing a non-water-soluble drug in an aqueous medium. However, in such a system, benzalkonium chloride (BAC—i.e., the monomeric compound) is ineffective at the standard concentration (0.01%) because HP-β-CD forms a complex with BAC. Therefore, when HP-β-CD is present in the formulation, a different anti-microbial agent such as phenylmercuric acetate has to be used.

The experiments for evaluating PBAC beads in levocabastine solution, which contained 0.05% levocabastine, 7.5% HP-β-CD, 1.0% boric acid, 0.25% sodium chloride and 0.01% EDTA, were performed (PET #'s 2538 and 2539). The results are displayed in Table 3, along with the results using no preservative and using BAC. The PBAC resin (Example 3) passed the abbreviated version of preservative effectiveness test by both the USP and the BP B criteria. The abbreviated version of preservative effectiveness test was carried out using only two microorganisms (S. aureus and A. niger) instead of the required five organisms, but the two were the most difficult ones. Therefore, if the system passes for the two, it will most likely pass the full preservative effectiveness test. The results are significant since benzalkonium chloride (BAC) is ineffective in the levocabastine solution unless a high concentration (five times the standard BAC concentration) is used. At such a high concentration, BAC could very well cause toxic effects to the patient. As the data show, PBAC is effective in the presence of HP-β-CD, and, moreover, PBAC can provide a preservative free solution to the patient. Therefore, PBAC gives wide opportunities to develop various formulations.

Other cyclodextrin derivatives that can be used as complexing agents for difficultly soluble pharmaceutical products include other hydroxyalkyl cyclodextrins, alkyl cyclodextrins, carboxyalkyl cyclodextrins, and other cyclodextrin ether derivatives, such as are disclosed in U.S. Pat. No. 3,459,731, EP-A-149,197, EP-A-197,571, EP-A-146,841 and EP-A-147,685.

In addition to levocabastine, an anti-allergy drug, a wide variety of drugs can be used in the aqueous drug composition of the invention. These include steroids and other anti-inflammatory drugs, anti-glaucoma drugs, drugs used to dilate the pupil, and other aqueous ophthalmic drug compositions. In addition, "aqueous drug composition" includes aqueous ophthalmic compositions that are intended for use in lubricating and/or hydrating the eye, such as Hypotears®.

TABLE 3

Efficacy of PBAC in the Levocabastine Solution[a]

| PET # | BAC (%) | PBAC g/mL | PET Results[b] USP | BP/B | J&J |
|---|---|---|---|---|---|
| 2540[c] | 0 | 0 | P | F | F |
| 2444 | 0.005 | 0 | F | F | F |
| 2445 | 0.01 | 0 | F | F | F |
| 2446 | 0.02 | 0 | F | F | F |
| 2447 | 0.05 | 0 | P | P | P |
| 2538/2539[c] | 0 | 0.2 | P | P | F |

[a]0.05% levocabastine, 7.5% hydroxypropyl-β-cyclodextrin (HP-β-CD), 1.0% boric acid, 0.25% sodium chloride, and 0.01% EDTA.
[b]P: passed, F: failed.
[c]Preservative effectiveness test was carried out by an abbreviated version using only S. Aureus and A. Niger.

PRESERVATION EFFICACY TEST RESULTS

| Challenge Micro-organisms | Require-ment Standard | Initial Inocu-lation | Reduction of microorganism from initial challenge (Log) | | | |
|---|---|---|---|---|---|---|
| | | | 6 Hrs | 24 Hrs | 7 Days | 14/21/28 Day |
| Bacteria: | | | | | | |
| Staphylococcus aureus | B.P. | $10^5$–$10^6$ | ≧2 Log NR | ≧3 Log ≧1 Log | NI ≧3 Log | NOR - A NI - B |
| Pseudomonas aeruginosa | J.J. | $10^5$–$10^6$ | NR | NR | NOR | NOR |
| Escherichia coli | U.S.P. | $10^5$–$10^6$ | NR | NR | NR | ≧3 Log |
| Yeast & Mold: | | | | | | |
| Aspergillus niger | B.P. | $10^5$–$10^6$ | NR NR | NR NR | ≧2 Log NR | NI - A ≧1 Log - B |
| | J.J. | $10^5$–$10^6$ | NR | NR | ≧2 Log | ≧2 Log |
| Candida albicans | U.S.P | $10^5$–$10^6$ | NR | NR | NR | NI |

B.P. - British Pharmacopoeia for ophthalmic preparation (1993)
J.J. - Johnson & Johnson Preservative Requirement for ophthalmic preparation
U.S.P. - United States Pharmacopoeia for all multiple-dose pharmaceuticals
NR - No requirement
NOR - No microorganism recovered per mL
NI - No increase
A - Recommended efficacy to be achieved by B.P. (1993)
B - In justified cases where the A criteria cannot be attained, for example, for reasons of a increased risk of adverse reaction, the B criteria must be satisfied (1993-B.P.)
3 Log Reduction - 0.1% of challenge population
2 Log Reduction - 1% of challenge population
1 Log Reduction - 10% of challenge population

What is claimed is:

1. A package containing an aqueous drug composition comprising an insoluble resin, wherein said insoluble resin comprises benzalkonium units in an amount sufficient to inhibit growth of microbes in said aqueous drug composition, wherein said insoluble resin comprising benzalkonium units is a polymer containing repeating units of the formula:

—[$CH_2$—$CH(Ar)$]— wherein Ar=a group of the formula:

-Phe-$CH_2$—$N^+(CH_3)_2$R X$^-$ wherein R=long chain alkyl, Phe=phenylene, and X$^-$ is a pharmaceutically acceptable counter anion.

2. The package of claim 1 wherein the aqueous drug composition is free of soluble quaternary ammonium antimicrobial agents.

3. The package of claim 1 wherein the benzalkonium units are benzalkonium halide units.

4. The package of claim 3 wherein the halide is chloride.

5. The package of claim 1 wherein the aqueous drug composition includes hydroxypropyl-β-cyclodextrin.

6. The package of claim 2 wherein the aqueous drug composition includes hydroxypropyl-β-cyclodextrin.

7. The package of claim 3 wherein the aqueous drug composition includes hydroxypropyl-β-cyclodextrin.

8. The package of claim 4 wherein the aqueous drug composition includes hydroxypropyl-β-cyclodextrin.

9. The package of claim 1 wherein the aqueous drug composition includes levocabastine.

10. The package of claim 2 wherein the aqueous drug composition includes levocabastine.

11. The package of claim 3 wherein the aqueous drug composition includes levocabastine.

12. The package of claim 4 wherein the aqueous drug composition includes levocabastine.

13. The package of claim 5 wherein the aqueous drug composition includes levocabastine.

14. The package of claim 6 wherein the aqueous drug composition includes levocabastine.

15. The package of claim 7 wherein the aqueous drug composition includes levocabastine.

16. The package of claim 8 wherein the aqueous drug composition includes levocabastine.

17. The package of claim 1 wherein X$^-$ is Cl$^-$.

18. The package of claim 1 wherein R=$C_{8-18}$alkyl.

19. The package of claim 1 wherein the aqueous drug composition includes a cyclodextrin complexing agent for said drug.

* * * * *